(12) United States Patent
Sidler (10) Patent No.: US 7,993,402 B2
(45) Date of Patent: Aug. 9, 2011

(54) FILLER, SUPPLY DEVICE AND METHOD FOR FORMING A SUPPORT STRUCTURE IN A BONE CAVITY

(75) Inventor: Bruno Sidler, Menziken (CH)

(73) Assignee: Hkross AG, Schaffhausen (CH)

( * ) Notice: Subject to any disclaimer, the term of this patent is extended or adjusted under 35 U.S.C. 154(b) by 0 days.

(21) Appl. No.: 11/572,035

(22) PCT Filed: Jul. 14, 2005

(86) PCT No.: PCT/EP2005/007936
§ 371 (c)(1),
(2), (4) Date: Jan. 12, 2007

(87) PCT Pub. No.: WO2005/094735
PCT Pub. Date: Oct. 13, 2005

(65) Prior Publication Data
US 2007/0260313 A1    Nov. 8, 2007

(30) Foreign Application Priority Data

Jul. 14, 2004  (EP) .................................. 04405451

(51) Int. Cl.
*A61F 2/44* (2006.01)
*A61F 2/28* (2006.01)
*A61F 2/46* (2006.01)
(52) U.S. Cl. ..................... 623/17.11; 623/16.11; 606/92
(58) Field of Classification Search ............... 623/11.11, 623/16.11, 17.11, 17.16; 606/92–94
See application file for complete search history.

(56) References Cited

U.S. PATENT DOCUMENTS

| 2,870,668 | A | * | 1/1959 | Flahaut .......................... 411/436 |
| 5,676,700 | A |   | 10/1997 | Black et al. |
| 6,395,007 | B1 | * | 5/2002 | Bhatnagar et al. ............... 606/94 |
| 6,582,439 | B1 |   | 6/2003 | Sproul |
| 2003/0055511 | A1 |   | 3/2003 | Schryver et al. |
| 2004/0010314 | A1 | * | 1/2004 | Matsuzaki et al. ......... 623/17.11 |
| 2004/0024410 | A1 | * | 2/2004 | Olson et al. ..................... 606/93 |
| 2004/0052829 | A1 |   | 3/2004 | Shimp |
| 2004/0067120 | A1 | * | 4/2004 | Speer .............................. 411/14 |
| 2004/0073440 | A1 |   | 4/2004 | Garbers et al. |
| 2004/0097930 | A1 |   | 5/2004 | Justis et al. |
| 2005/0278023 | A1 | * | 12/2005 | Zwirkoski .................. 623/11.11 |
| 2006/0072756 | A1 |   | 4/2006 | Leimgruber et al. |
| 2006/0085081 | A1 | * | 4/2006 | Shadduck et al. ......... 623/23.76 |

FOREIGN PATENT DOCUMENTS

| WO | 01/54746 | 8/2001 |
| WO | 2004/041075 | 5/2004 |
| WO | 2004/047689 | 6/2004 |

OTHER PUBLICATIONS

Cunin G, et al., "Experimental Vertebroplasty Using Osteoconductive Granular Material", Spine, Philadelphia, PA, US; vol. 25 No. 9; May 1, 2000; pp. 1070-1076; abstract.

* cited by examiner

*Primary Examiner* — Corrine M McDermott
*Assistant Examiner* — Megan Wolf
(74) *Attorney, Agent, or Firm* — Fish & Associates, PC (57) ABSTRACT

The invention relates to dry free-flowing filler (1) for forming a support structure in a bone cavity (4*a*). The filler comprises a plurality of biocompatible support bodies (2) which are resistant to deformation or fracture under the physiological loads usually occurring in the bone cavity (4*a*). Said support bodies (2) have a size between 2 mm and 10 mm and an axis (A) and two opposite abutments (2*g*) spaced apart in the direction of the axis (A).

33 Claims, 7 Drawing Sheets

FILLER, SUPPLY DEVICE AND METHOD FOR FORMING A SUPPORT STRUCTURE IN A BONE CAVITY

The present invention relates to a filler means for the formation of a sup-port structure in a bone cavity. The invention furthermore relates to a feeding device for the filling of a filler means into a bone cavity. Furthermore the invention relates to a method for the filling of a bone cavity with a support structure.

The invention relates to the treatment of bones of humans or animals.

The increasing aging of society leads to an above average increase in diseases of the locomotion and support apparatus, in particular of the bones. Bones can be damaged or weakened in the most diverse manners, for example by trauma, infection, wear, tumor growth or degenerative illnesses such as osteoporosis. In older humans, osteoporosis, that is to say the depletion of the spongiosa, represents a problem because in this way the load carrying ability of the bone is weakened, which has the consequence that bone fractures increasingly occur, above all in the spinal column, at the neck of the femur and at the wrist. A treatment of such bone fractures is difficult, in particular when degenerative changes in an advanced state are present. For the fixation of such bone fractures external or internal splints (plates, screws, implants) are normally used which hold the bone together until it has healed. Such splints cannot, however, be used for all bones. Thus, for example, for the spine the so-called vertebroplastie is used for the treatment of a degenerated or partly fractured vertebral body and the damaged vertebral body is filled with bone cement. The use of bone cement in vertebral bodies however has various disadvantages, in particular that the bone cement can emerge in uncontrolled manner via veins or small bone defects in the vertebral body and can thereby cause damage in adjacent anatomic structures, such as for example on escaping into the spinal passage. Further disadvantages of bone cement are that it warms up strongly during hardening which can damage surrounding tissue or indeed nerves, that the bone cement must be very quickly processed, that no bone can grow in the bone cement and that the bone cement becomes brittle in the course of time.

The document US 2004/0052829 discloses a method for treatment of porous vertebral bodies, in particular of vertebral bodies with an osteoporotic fracture. For this purpose, a biocompatible liquid carrier substance such as water is used which is enriched with biocompatible support bodies. The disadvantage of this method is the fact that a balloon-like container is required which must first be introduced into the vertebral body and which is thereafter filled with the carrier substance containing the support bodies. The balloon-like container is required in order to ensure that both the liquid carrier substance and also the support bodies contained therein remain within the vertebral body. If no balloon-like container were used, then the known danger of outflow would also exist in this method in which the liquid carrier substance and also the support bodies contained therein, which have a size in the micrometer range, can escape out of the damaged vertebral body and can damage adjacent tissue in an uncontrolled manner or propagate in the human body. The known method thus has the disadvantage that it is complicated and expensive to introduce the balloon-like container into the vertebral body, that this can be damaged during the introduction or by the support bodies, so that the carrier substance can flow out and that the vertebral body can not be ideally filled because the balloon-like container "inflates" during the feeding of the liquid carrier substance and thus takes up more space than is necessary per se for the support bodies.

The document US 2004/0097930 discloses a further method for the treatment of vertebral bodies. This method discloses spherical bodies which are introduced into the internal space of the vertebral body. After the operation has been completed, the spinal column is loaded in the axial direction, that is to say in the direction of extent of the spinal column. This loading has the consequence that the ball-like bodies are urged radially to the axis of the spinal column, with the vertebral body bodies sinking in and being deformed. In an unfavorable case the ball-like bodies penetrate the jacket of the vertebral body and can thus be distributed in an uncontrolled manner in the human body. The document moreover discloses four-cornered bodies which are to be introduced into the inner space of the vertebral body. These four-cornered bodies mutually block one another during the supply such that these bodies cannot be introduced into the interior space of vertebral body. The disclosed method thus has the disadvantages that the bodies introduced into the vertebral body want to escape under load and/or that the bodies to be introduced cannot be supplied to the vertebral body.

It is thus the object of the present invention to propose a more advantageous, implantable and in particular injectable filler means which permits defective bones, in particular vertebral bodies, to be ideally supplied in such a way that the bones are able to carry the physiological loads that are present from the time of the implantation onwards.

This object is satisfied with a filler means capable of dry flow having the features of claim 1. The subordinate claims 2 to 24 relate to further advantageously designed filler means. The object is further satisfied with a feeding device for the introduction of the filler means having the features of claim 25. The subordinate claims 26 and 30 relate to further advantageous embodiments. The object is further satisfied with a method for the filling of a bone cavity with support bodies having the features of claim 31. The subordinate claims 32 to 40 relate to further advantageous method steps. The object is further satisfied with a system having the features of claim 41.

The object is in particular satisfied with a filler means capable of dry flow for the formation of a support structure in a bone cavity, with the filler means including a plurality of biocompatible support bodies, which are resistant to deformation or fracture under the physiological loads which normally occur in the bone cavity, with the support body having a size between 2 mm and 10 mm and an axis as well as two oppositely disposed abutment locations which are spaced apart in the direction of the axis. The abutment locations are preferably designed as abutment surfaces.

The expression "capable of dry flow" signifies that the filler means can be injected, but without using any sort of fluid carrier substance which could endow the support bodies with flow characteristics. The support bodies are selected to be sufficiently large in that they can all be displaced in a cannula, while lying behind one another within the cannula, in that a pressure is exerted on the rearmost support body and this force is transmitted to all of the support bodies located in the cannula so that the support bodies are moved in the cannula towards the tip of the cannula. The support bodies are aligned within the cannula in such a way that the abutment locations of two support bodies following one another each contact one another. These support bodies have dry flowing characteristics in that they have a type of flow characteristics within the cannula without a carrier substance, in that the support bodies, in similar manner to an injection, can be fed to a bone cavity via the cannula.

The expression "support body" designates a body which is able to carry the forces which occur in a vertebral body without being substantially deformed or indeed destroyed. A plurality of biocompatible materials are known from which such a support body can be manufactured. For example the support body can be manufactured from

- ceramic materials, in particular calcium phosphate/hydroxylapatite, aluminum oxide, zirconium oxide, ATZ ceramic (aluminum zirconium oxide), bioactive glasses, glass ceramic materials, porcelain or a combination thereof or
- metallic materials in particular titanium, tantalum, stainless steel, steel alloys such as cobalt chrome alloy, titanium alloys such as titanium nickel alloy or titanium aluminum niobium/vanadium alloy or a combination thereof, or
- polymers, in particular polymethyl methacrylate (PMMA), polyetherether ketone (PEEK), polyethylene (PE), polyethylene terephthalate (PET) or a combination thereof, or
- biodegradable polymers such as polylactate.

The filler means in accordance with the invention including a plurality of biocompatible support bodies has the advantages that no balloon or other bounding means is required in the bone cavity because, on the one hand, the filler means has no carrier substance such as a liquid which could run out because the filler means is capable of dry flow within the cannula and, on the other hand, because the filler means consists of individual relatively large support bodies which, as a result of their size, can also hardly escape in uncontrolled manner from a severely damaged vertebral body, and which, as a result of their size, cannot become distributed in an uncontrolled manner in the body. The filler means in accordance with the invention is capable of dry flow and can thus be injected into a bone cavity with the aid of a cannula. The filler means in accordance with the invention is thus also suitable in particular for the medical care of bones which are difficult to access such as vertebral bodies.

In a particularly advantageous embodiment the support bodies are designed such that they can mutually wedge one another so that the support bodies which are located in the bone cavity are mutually wedged and thereby form a cohesive support structure. The support bodies are preferably wedged such that they form a self-stable support structure. This is in particular important for loaded spinal columns.

The filler means of the invention permits bone defects, such as fractured bones, in particular weakened, fractured or partly fractured vertebral bodies to be filled with a support structure consisting of individual support bodies. Moreover, vertebral bodies which have been partly fractured can be aligned again. The support structure endows the bone with a stability, transmits forces which occur and can moreover promote bone healing and/or bone formation. The support bodies can, moreover, be filled with a bone healing and/or bone forming substance and/or be coated or have a bone healing and/or bone forming surface structure. The filler means in accordance with the inventions can be introduced into the bone by means of a supply device comprising a small cannula, which enables a caring access to the bone. In an advantageous embodiment the feeding device includes a force measuring device in order to measure the force which acts the support element on occur during introduction in the feed direction. In this way an excessive force is avoided during the introduction. Hereby a breaking through of the outer wall of the vertebral body is avoided. Moreover, the doctor has available an indicator via the introduction force which is able to say something about the state of filling of the vertebral body. In a further advantageous embodiment the feeding device includes a drive device which actuates a plunger provided in the cannula. The drive device exerts a mechanical force on the plunger and on the support bodies arranged in front of it in the feed direction, for example a constant force, a tap or a vibration. In a further embodiment the feeding device has a plunger which extends up to and into the bone cavity with the tip of the plunger serving as a manipulation instrument in order to change the position of the support bodies located within the bone cavity, for example to align them.

The invention will be explained in detail in the following with reference to Figures. There are shown.

Figure 1:
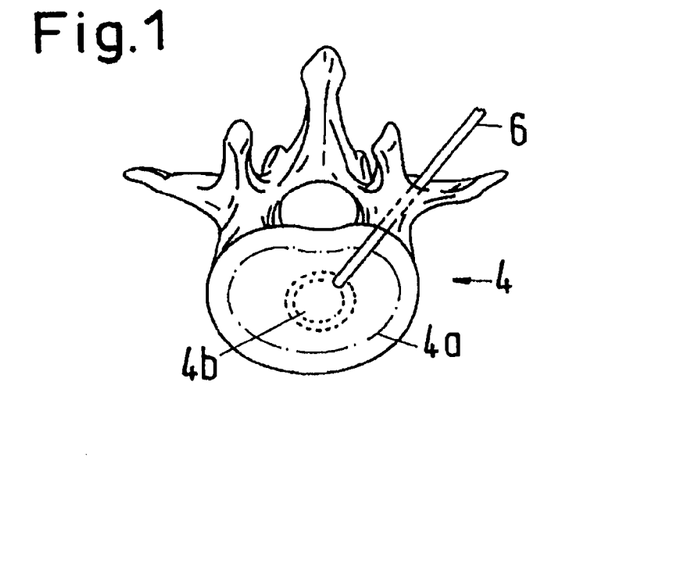
FIG. 1 a plan view of a vertebral body with an inserted cannula.

FIG. 1 shows in a plan view a bone 4, specifically a vertebral body having an internal bone space 4a. The term internal bone space 4a will be understood to mean the entire volume taken up by the bone 4. In the internal bone space 4a there is a bone cavity 4b into which a cannula 6 opens. The bone cavity 4b can for example have arisen because of degenerative processes, in particular osteoporosis. The bone cavity 4b can also be artificially produced or enlarged with a suitable instrument.

Figure 2:
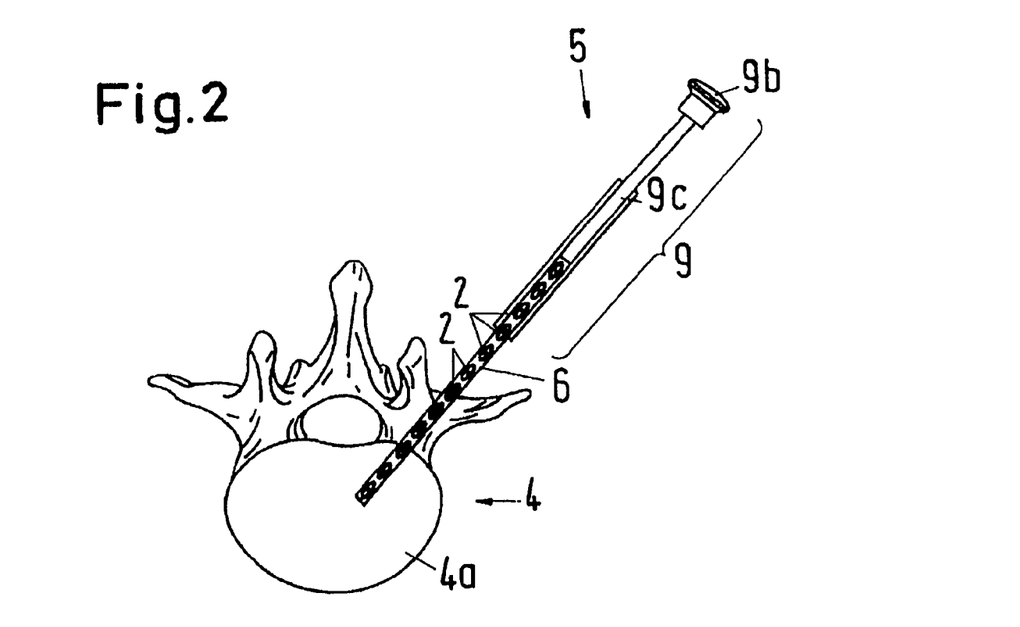
FIG. 2 a section through a vertebral body into which the filler means has been introduced.

FIG. 2 shows a vertebral body 4 having an internal bone space 4a and also a supply device 5 comprising a cannula 6, a pressing device 9 with an actuating handle 9b and a plunger 9c. The cannula 6 opens into the internal bone space 4a which in this embodiment has no bone cavity 4b. Biocompatible support bodies 2 are arranged behind one another in the inner space of the cannula 6 and of the pressing device 9 and are arranged substantially mutually touching one another so that the plunger 9c acting on the rearmost support body 2 drives all support bodies 2 in the direction of the internal bone space 4a. This makes it possible, if necessary, to transfer the force applied to the actuating handle 9b via the support bodies 2 up to the support bodies 2 located at the tip of the cannula 6, so that these penetrate into the internal bone space 4a with a corresponding force and thereby form a bone cavity 4b during the penetration. The inner diameter of the cannula 6 and also of the pressing device 9 are designed and matched with respect to the outer diameter of the support bodies 2 in such a way that the support bodies 2 are arranged behind one another in the flow direction, i.e. towards the outlet opening of the cannula 6, which has the consequence that the totality of the support bodies 2 form a filler means 1 capable of dry flow which has flow characteristics without any form of lubricant, in that support bodies 2 can be supplied with a syringe-like device shown in FIG. 2 to the internal bone space 4a. The cannula 6 can also extend in curved manner or consist of a flexible or solid material.

Figure 3:
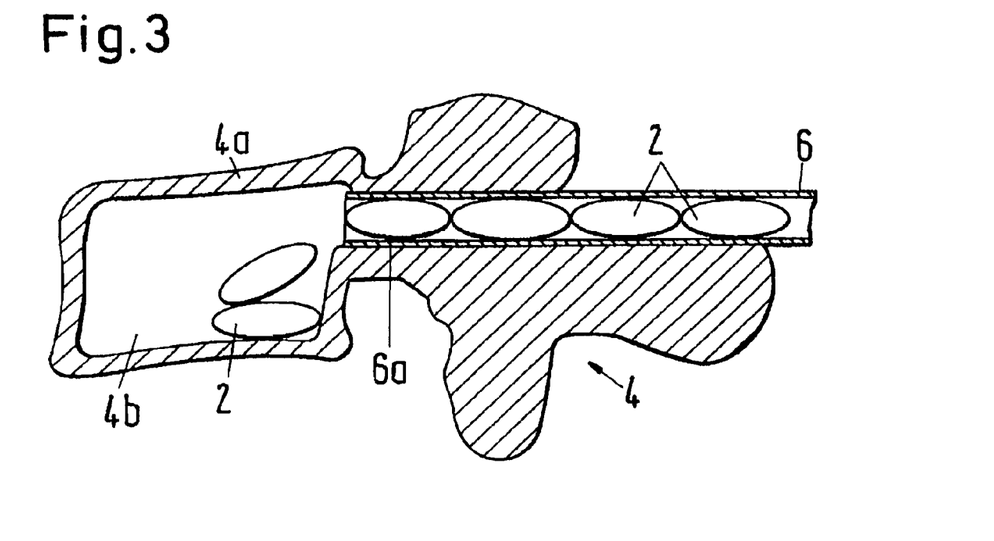
FIG. 3 a section through the vertebral body and also the cannula in accordance with FIG. 2.

The vertebral body 4 shown in FIG. 3 in section has a bone cavity 4b which was produced prior to the insertion of the support bodies 2 with a special instrument. Thereafter the tip 6a of the cannula 6 is driven forward up to the bone cavity 4b and thereafter the support bodies shown in a side view are introduced individually following one another and in a defined mutual position so they become distributed in random manner in the bone cavity 4b. The cannula 6 has a round internal cross-section so that each support body 2, which are all identically designed, has an elongate spherically extending outer contour. The support body 2 has a maximum dimension between 2 mm and 10 mm. The support bodies 2 are designed as solid bodies. All support bodies 2 are identically designed with respect to dimension and shape.

Figure 4:
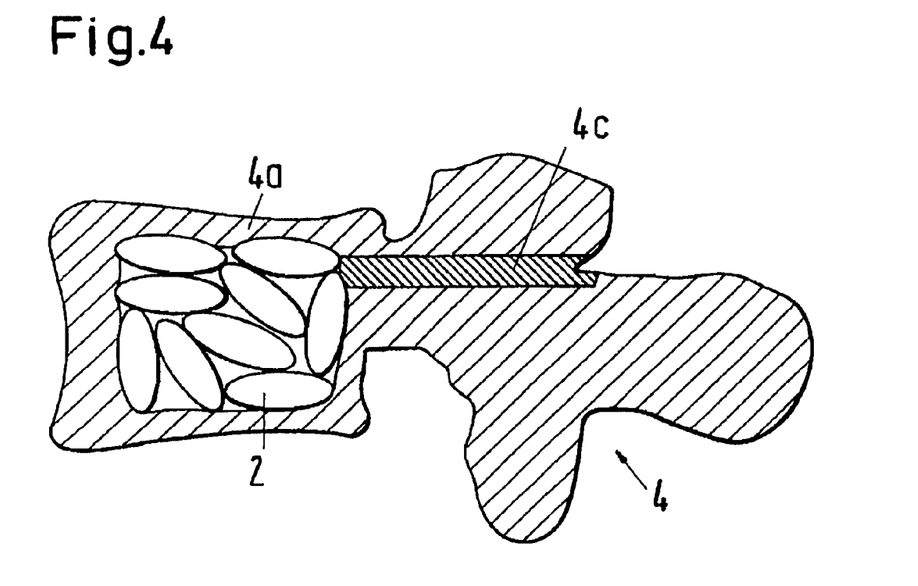
FIG. 4 a section through the vertebral body with a fully introduced filler means.

FIG. 4 shows the vertebral body shown in FIG. 3 with a bone cavity 4b completely filled with support bodies 2, with the support bodies 2 contacting one another at different points and thereby being entrapped in the bone cavity 4b so that the totality of these support bodies 4 form a load bearing support structure. The access passage to the bone cavity 4b is closed with a plug 4c after the introduction of the support bodies 2.

Figure 5A:
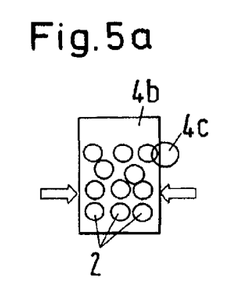
FIGS. 5a to 5e schematic representations of differently shaped support structures.
Figure 5B:
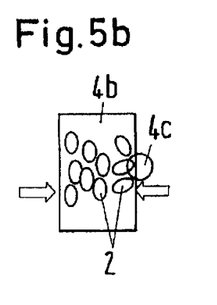
Figures 5C, 5D:
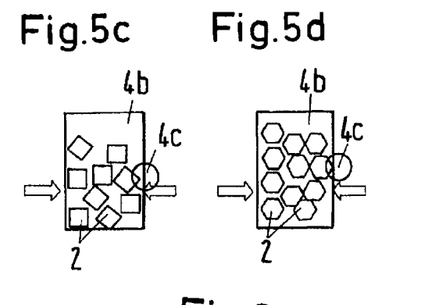
Figure 5E:
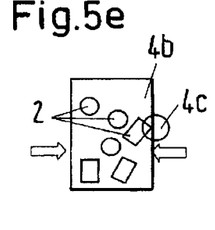

An internal bone space 4a or a bone cavity 4b can be filled with the most diversely shaped support bodies 2. FIG. 5a shows schematically a bounded bone cavity 4b with an inlet opening 4c through which the ball-like support bodies are introduced. FIG. 5b shows an ellipsoidally designed support body 2. An advantage of the support bodies shown in FIGS. 5a and 5b with a spherical outer contour is the fact that they can be mutually displaced with a low expenditure force so that the support bodies 2 can very readily fill the volume of the bone cavity 4b. The FIGS. 5c and 5d show support bodies 2 with an edge-like outer contour, with the side surfaces of the support bodies 2, which converge at an angle, being able to exert a wedge action so that the support bodies 2 located in the bounded bone cavity 4b can become mutually wedged in an advantageous embodiment such as is shown in FIG. 5c, with larger intermediate spaces resulting between the support bodies 2 into which the bone can grow. The totality of the support bodies 2 in turn forms a mechanically loadable support structure. In contrast to the support bodies 2 shown in FIGS. 5a to 5d, which are respectively identical having regard to their shape and size, the support bodies 2 could also have different shapes and/or sizes within the bone cavity 4b as shown in FIG. 5e.

Figure 6A:
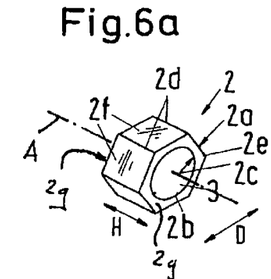
FIGS. 6a to 6d support bodies with cornered outer contours.
Figure 6B:
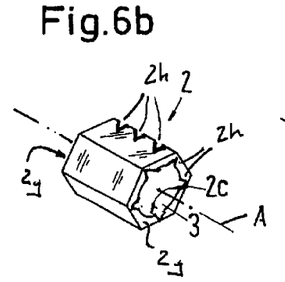
Figure 6C:
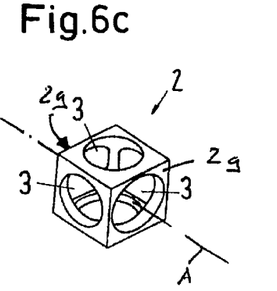
Figures 6D, 6E, 7D:
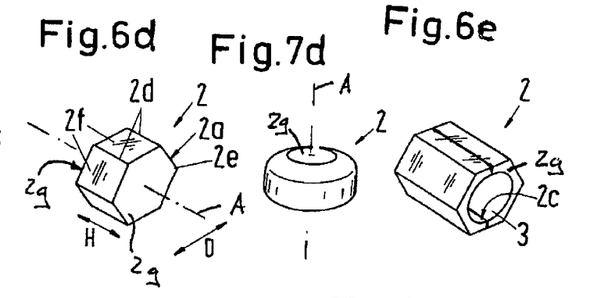
FIGS. 7a to 7d support bodies with rounded outer contours.
Figure 7A:
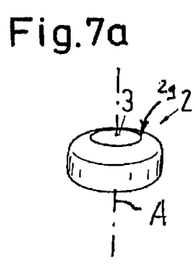
Figure 7B:
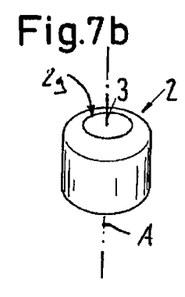
Figure 7C:
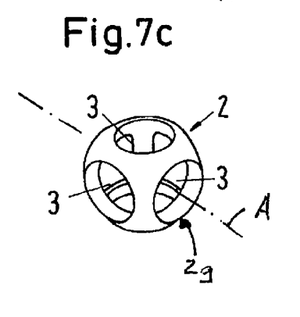

The FIGS. 6a-6d and 7a-7d show support bodies 2 which have an axis A, with each support body 2 having two oppositely disposed abutment locations 2g which are spaced apart in the direction of the axis A. The abutment locations 2g of FIGS. 6a-6d and also of FIG. 7d are designed as abutment surfaces 2g, whereas the abutment locations 2g of FIGS. 7a-7c are designed as rings with a small mutual contact surface. In the embodiments of FIGS. 6a-6e the abutment locations 2g extend perpendicular to the axis A. In the embodiments in accordance with FIGS. 7a-7d the abutment locations 2g have a circular or spherical or curved extent. The abutment locations 2g of the embodiments of FIGS. 7a-7c can also be of ring-like shape extending perpendicular to the axis A. The support bodies 2 have, as shown in FIGS. 6a-6c, 7a-7c, a recess disposed perpendicular to the abutment point 2g. This cut-out 2c can be designed as a recess or also as a through-going, open, internal cavity 3 which extends between two oppositely disposed abutment locations 2g and opens into the oppositely disposed recesses 2c. The cut-out 2c can be eccentric or, as shown in FIGS. 6a-6c, 7a-7c, extend concentrically to the axis A. The support bodies 2 can also consist of two or also more partial bodies, for example of four partial bodies which can move independently of one another in the bone cavity.

The FIGS. 6a-6b and 6c and also 7a, 7b and 7c show support bodies 2 having an open inner cavity 3. An open inner cavity 3 will be understood to be a hollow cavity in the support body 2 which is open towards the outside, in contrast to a closed cavity which is arranged completely within the interior of the support body 2 without having an opening towards the outside. These support bodies 2 also have a maximum size in the range between 2 mm and 10 mm. Each support body 2 includes a total volume which corresponds to the volume of the material of the support body 2 and also its inner cavity 3. The volume of the inner cavity is larger than 30% of the total volume, preferably larger than 50% and can amount to up to 90%. The size of the maximum possible volume of the internal cavity 3 is dependent on the maximum pressure forces acting on the support body 2. These pressure forces are dependent on the specific internal bone space 4a and/or the bone 4 in which the support structure is formed. The load carrying ability of the support body 2 is naturally dependent on the material used. If the support body 2 is for example made of metal the internal cavity 3 can be made relatively large and the support bodies 2 are nevertheless resistant to the pressure forces that are acting. If the support body 2 is made of a material such as bio-glass or a resorbable substance, the internal cavity 3 must be made smaller percentage-wise in accordance with the material characteristics in order to provide the support body 2 with a sufficiently large load carrying force. This internal cavity 3, in particular a relatively large internal cavity 3 percentage-wise, has the advantage that it can be filled in the course of time by growing bone material. In a particularly advantageous design the internal cavity 3 of the support body 2 is at least partly filled prior to its introduction with an osteo-inductive and/or osteo-conductive substance, in particular a bone growth promoting protein or calcium sulphate or a combination of these or further substances. Thanks to such filled support bodies 2 it is possible to feed both a support structure and also osteo-inductive and/or osteo-conductive substances to the internal bone space 4a by means of the filler means 1 capable of dry flow and consisting of a plurality of support bodies 2. This design has the advantages that the filler means 1 can be supplied to the internal bone space 4a dry so that no danger exists of anything running out through cracks, gaps and openings which may possibly be present in the bone. Moreover, the osteo-inductive substance brings about bone growth so that the hollow spaces 3 and the intermediate spaces which result through the support bodies 2 are advantageously increasingly filled with growing bone. Since the support bodies 2 in the internal bone space 4a are arranged aligned at random, that is to say the hollow spaces 3 extend in random directions and also the intermediate spaces extend in random directions and have a size determined by chance, the support bodies 2 actually form a support structure similar in the broader sense to spongiosa, in particular when the volume of the internal cavity 3 amounts to more than 50% of the total volume. When, in the course of increasing healing, the hollow cavities 3 and the intermediate spaces are filled with growing spongiosa, then a support structure forms in the internal bone space 4a which is partly comparable with a healthy bone, with randomly aligned support bodies 2 the hollow cavities and intermediate spaces of which have spongiosa growing through them.

The inner cavity 3 of the support bodies 2 in accordance with FIGS. 6a, 6b, 6c, 7a, 7b, 7c is made cohesive and non-porous so that the internal contour 2b bounds a relatively large internal cavity 3 laterally. The internal cavity 3 in accordance with the FIGS. 6a, 6b, 7a, 7b is of cylindrical shape, extends concentric to the axis A and has a circular opening 2c. The angle between the internal wall of the internal cavity 3 and the abutment location 2g thus amounts to 90 degrees at the circular opening 2c. The circular opening 2c can, as shown in FIG. 6b, have blocking points 2h, for example a plurality of notches arranged in the peripheral direction. The opening 2c can have the most diverse shapes and can for example also be formed as a triangle, tetragon or as a frequency polygon. The internal cavity 3 could have the same shape as given by the opening 2c, with the internal cavity 3 extending in the axial direction A over the entire length of the support body 3. The support bodies 2 in accordance with FIGS. 7a, 7b are made essentially circular. The support bodies 2 in accordance with the FIGS. 6a, 6b have a polyhedral outer contour in the peripheral direction with edges 2d extending parallel to the axis A and six surfaces 2f which extend in a mutually wedge-shaped manner which respectively meet at an edge 2d or corner 2e. The support body 2 has a preferably 3-cornered to 10-cornered outer contour in the peripheral direction, in particular a 4-cornered, 5-cornered or 6-cornered outer contour. The edges 2d can have blocking points 2h, as shown in FIG. 6b, such as notches.

The embodiment in accordance with FIG. 7a has a spherical, in particular ball-shaped or episoidal outer contour. The support bodies 2 in accordance with the FIGS. 6b and 7b are essentially of hollow cylindrical shape. The support bodies 2 in accordance with FIGS. 6c and 7c have essentially a cuboid or spherically extending outer contour. The support bodies 2 in accordance with FIGS. 6d and 7d have, in distinction to the embodiment of FIGS. 6a, 7a, no hollow cavity 3.

Figure 8A:
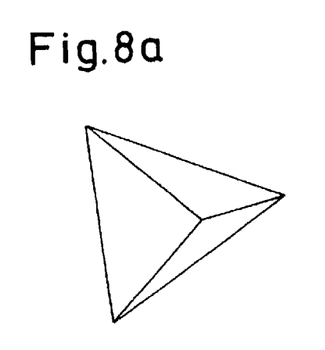
FIGS. 8a to 8d support bodies with polyhedral outer contours.
Figure 8B:
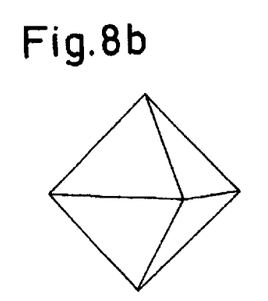
Figure 8C:
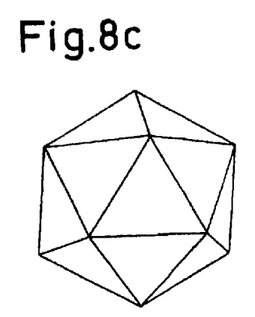
Figure 8D:
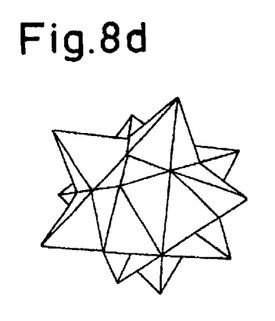

The FIGS. 8a to 8d show further embodiments of support bodies 2 with polyhedrally extending outer contours, with the illustrated support bodies 2 not having any hollow space 3. The support bodies 2 could however also have a cavity 3. FIG. 8a shows a tetrahedron, FIG. 8b an octahedron, FIG. 8c an ikosahedron and FIG. 8d a small star-shaped dodecahedron. The two oppositely disposed abutment locations 2g spaced apart in the direction of the axis A, which are necessary in order to forward this embodiment in a cannula in the direction of the axis A, are not shown in this embodiment.

Figure 9:
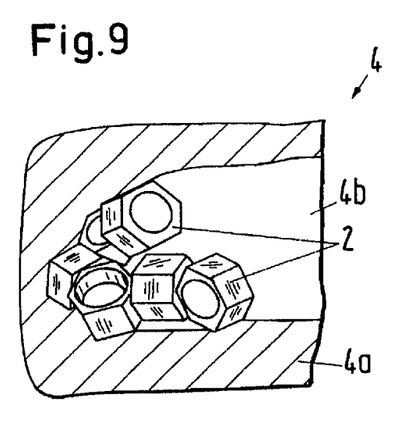
FIG. 9 a further embodiment of a bone cavity partly filled with filler means.
Figure 17:
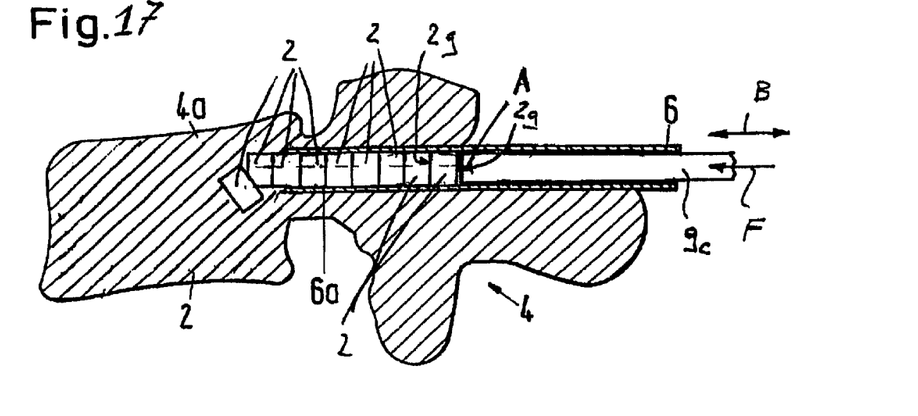
FIG. 17 a longitudinal section through a further vertebral body with a feed apparatus and support bodies which are to be introduced.

In an advantageous design, as shown in FIG. 6a, the support body 2 has an outer diameter D and a height H extending orthogonal to it, i.e. in the direction of the axis A, with the outer diameter D preferably amounting to 1.5-times the height H. The support bodies 2 have a surface formed such that the surface of a filling body 2 filled into the bone cavity can project into the cut-out of an adjacently disposed support body 2 as shown in FIG. 9. In an advantageous embodiment the support bodies 2 have surfaces and also recesses designed such that mutual wedging or jamming occurs between the surfaces which project into the cut-outs and the cut-out, in order to form within the internal bone space 4a a preferably cohesive and in particular self-stable support structure. The surface of the support body 2 which is radial to the axis A thus preferably has shapes from the group: corner, edge, tip, recess, aperture or a combination thereof in order to bring about a mutual wedging and jamming of the support bodies 2. In an advantageous embodiment the support body 2 has, as shown in FIG. 6a, a form similar to a threaded nut with a multi-cornered outer contour extending in the direction of extent of the axis A with surfaces 2f which mutually extend in wedge-like manner and pronounced edges 2d and corners 2e as well as an inner cavity 3 with an opening 2c of relatively large diameter. FIG. 9 shows a first bone cavity 4b partly filled with such threaded nut-like support bodies 2. It is evident from this arrangement of the support bodies 2 how the support bodies 2 are mutually wedged in that the outer contour partly penetrates via the opening 2c into the internal space 3, so that the support bodies 2 are mutually wedged and in this way form a mechanically at least cohesive support structure. As soon as the entire bone cavity 4b is completely filled with the support bodies 2 the support structure formed in this way can carry the load acting on the bone 4 from the outside essentially as a composite assembly. The filler means 1 introduced into the internal space 4a of a vertebral body, comprising a plurality of, for example, 20 to 50 support bodies 2, preferably forms a self-stable support structure in that the individual support bodies 2 are mutually wedged in such a way that the support structure which is formed is held together by a force acting in the direction of extent of the spinal column. If the internal space 4a were filled with spherical support bodies, then these would attempt, with a force acting in the direction of extent of the spinal column, to escape in a direction perpendicular to the force, which produces an excessive force on the outer jacket of the vertebral body or can indeed lead to damage to the outer jacket and to the escape of the support bodies. Through the mutual wedging of the support bodies this excessive force acting on the outer jacket is considerably reduced. The arrangement of the support bodies 2 shown in FIG. 9, or a very similar arrangement, also results when these are pressed into the vertebral body as shown in FIG. 17.

Figure 14:
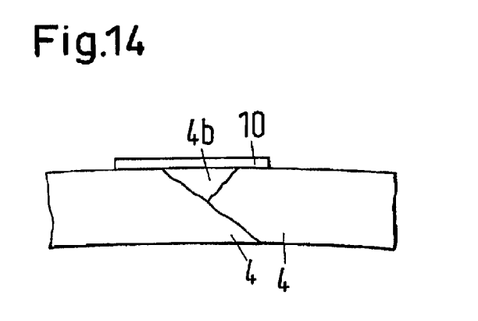
FIG. 14 a broken bone having a bone cavity.

FIG. 14 shows a broken bone 4, with a bone part missing at the position of the fracture. This part is covered over with a bone plate 10 so that a bone cavity 4b forms. A bone cavity 4b of this kind can also be filled with the above-described filler means 1 comprising support bodies 2.

Figure 10:
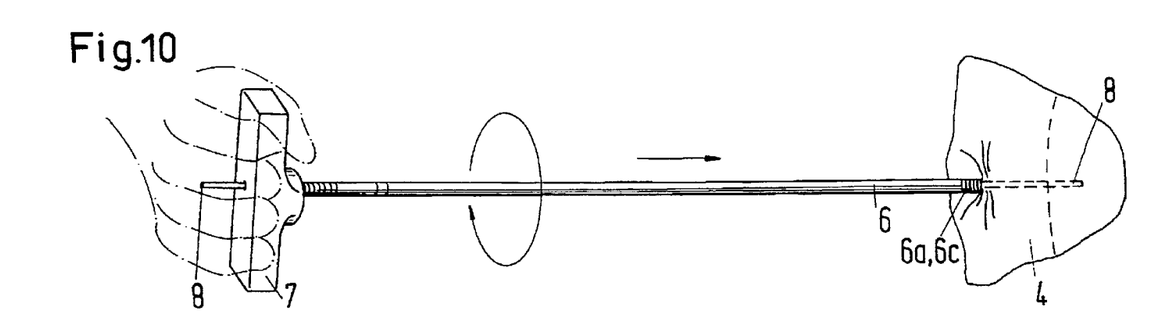
FIG. 10 the fastening of a cannula in a bone.
Figure 11:
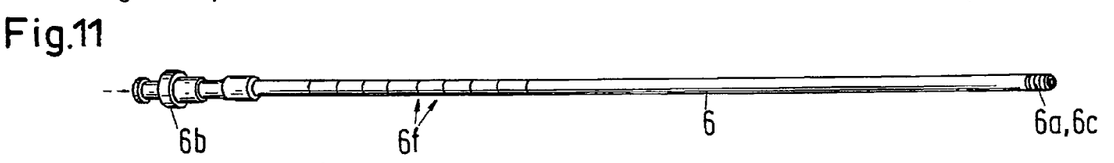
FIG. 11 a cannula.
Figure 12:
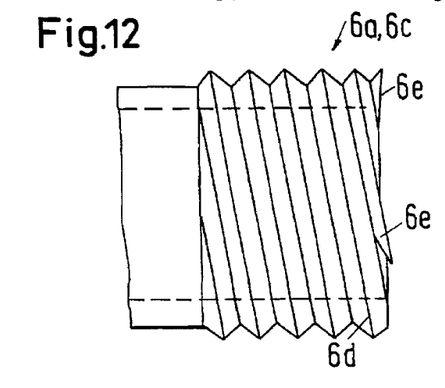
FIG. 12 a cannula tip.
Figure 13:
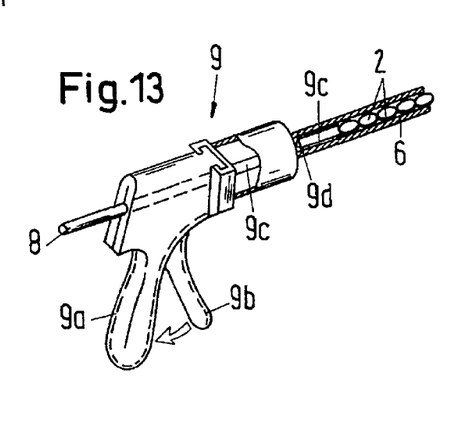
FIG. 13 a pressing apparatus.

FIG. 10 shows rigid cannula 6 with a cannula tip 6a formed as a cutting thread 6c. A Kirschner wire 8 extends within the cannula 6. The Kirschner wire 8 is first pushed into the bone 4 an order to determine the direction of extent of the cannula 6. Thereafter the tip 6a of the cannula 6 is screwed with a rotating movement into the bone 4 using the handle 7 so that the tip 6a and thus the cannula 6 is firmly anchored in the bone 4. Thereafter the handle 7 is removed. FIG. 11 shows the cannula 6 with the removed handle 7. The cannula 6 includes a connection part 6b for the handle 7 and for a pressing device 9 respectively. FIG. 12 shows an embodiment of a tip 6a of the cannula 6 in detail. The tip 6a has projecting cutting elements 6e and an outer thread 6d. FIG. 13 shows a pressing device 9 which is connected via the connection part 6b to the cannula 6. Prior to the connection the cannula 6 was filled with support bodies 2. The pressing device 9 includes a handle 9a and also an actuating grip 9b which acts on a plunger 9c in such a way that it moves a bit further into the cannula 6 at each actuation, so that the plunger 9c acting on the support bodies 2 presses the support bodies 2 which are arranged at the foremost position in the cannula 6 into the bone 4. The support bodies 2 thus flow into the bone 4 and in this way also form a bone cavity 4b therein as a result of the pressure and fill it with support bodies 2 so that a support structure is formed within the bone 4. The position of the plunger 9c can be read off with the aid of markings 6f applied to the cannula 6 from which it can be determined how many support bodies have been pressed into the bone 4. The support bodies 2 could also be arranged in an additional cannula which is introduced into the cannula 6 before the pressing device is connected to the cannula 6. Thus a second cannula which contains the support bodies 2 would be arranged within the cannula 6. In this way the cannula 6 could be loaded very simply with support bodies 2. The cannula containing the support bodies 2 must have an internal diameter matched to the size of the support bodies in such a way that the support bodies 2 can only be arranged following one another and are displaceable therein in order to supply the support bodies 2 one after the other to the internal bone space 4a. After the filling of the internal bone space 4a the pressing device 9 and the cannula 6 are removed and the hole in the bone is closed with a plug 4c as shown in FIG. 4.

Figure 15:
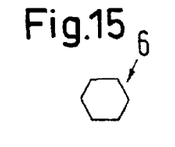
FIG. 15 a cross-section through a cannula.
Figure 16:
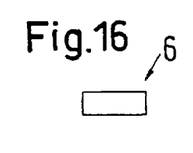
FIG. 16 a further cross-section through a cannula.

The cannula can not only have a round internal cross-section as shown in FIGS. 10 to 13 but also other cross-sectional shapes, for example a hexagonal internal cross-section as shown in FIG. 15, or a rectangular internal cross-section as shown in FIG. 16, which are for example suitable for the introduction of the support body 2 shown in FIG. 6a. The cannula 6 can also have further cross-sectional shapes matched to the respective contour of the support body 2 that is used.

The tip 6a of the cannula 6 can also be designed without a fastening means 6c. In particular, if a bone cavity 4b has already previously been formed, the support bodies 2 could also be fed, as shown in FIG. 2, to the bone cavity 4b with a device 9 similar to a syringe. In an advantageous method a group of support bodies, for example 5 or 10 support bodies following one another, is in each case supplied to the bone cavity 4b, thereafter the cannula 6 is removed and the support bodies 2, which are located in the bone cavity 4b, are additionally pressed in and compressed with the aid of a stuffing tool in order to thereafter replace the cannula at the bone 4 and to introduce a further group of support bodies 2 into the bone cavity 4b and to compress these again with the stuffing tool.

In a possible method step an osteo-inductive and/or osteo-conductive substance can be supplied after the support bodies 2 have been introduced into the internal bone space 4a, for example as a liquid or as a fluid, in order to fill the still present hollow cavities in the bone cavity 4b with this substance. The filler means 1 could also be supplied to the internal bone space 4a together with a fluid in that, for example, the support bodies 2 are made available together with the fluid, in particular mixed, in the pressing device 9 for introduction into the internal bone space 4a.

FIG. 17 shows a longitudinal section through a vertebral body 4 with a cannula 6 introduced into its internal bone space 4a. The support bodies 2 are designed as shown in FIG. 6a and have abutment locations 2g spaced apart in the direction of the axis A which lie against and mutually contact one another in the direction of the axis A. The support bodies 2 are pushed or pressed into the internal bone space 4a by means of a plunger 9c moved in the direction B on which a force F acts, with the support bodies 2 becoming randomly arranged in the internal bone space 4a and moreover forming a bone cavity 4b in the illustrated embodiment. The support bodies 2 located in the cannula 6 are arranged following one another and are otherwise identically arranged with respect to their position, if a cannula 6 in accordance with FIG. 15 is used. If the cannula 6 with a circular cross-section is used, then the support bodies 2 are also arranged following one another, but, with respect to their mutual position, could also be arranged rotated around the axis A. Since the support bodies 2 are arranged in defined manner inside the cannula 6 in the direction of extent of the axis A, i.e. in the direction of movement B, the support bodies 2 can be reliably displaced to the internal bone space 4a and with small resistance. The support bodies 2 can be structured radially to the axis A in the most diverse manner and for example have edges 2d, notches 2h or also projecting tips or cut-outs without these structures hindering the introduction of the support bodies through the cannula 6. The forces are reliably transmitted between the abutment locations 2g of the support bodies 2 and no mutual wedging of the support bodies takes place within the cannula 6 so that the support bodies can be reliably displaced into the internal bone space 4a. Within the internal bone space 4a the support bodies 2 order themselves arbitrarily, so that they mutually hinder one another with respect to their movement and mutually wedge and block one another.

Figures 19, 23:
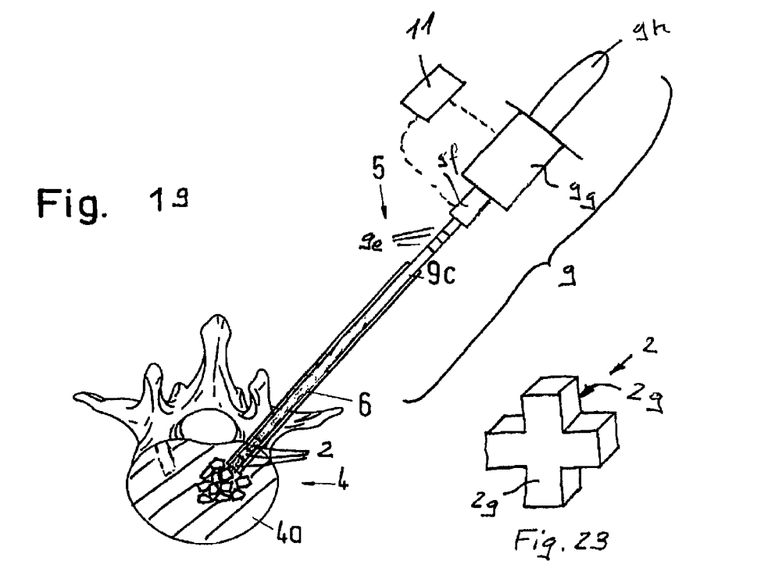
FIG. 19 a cross-section through a further vertebral body with introduced support bodies and also a plan view of a feeding device.
FIG. 23 a further embodiment of a support body.

FIG. 19 shows, in a cross-section of a vertebral body 4 a plurality of approximately 20 introduced support bodies 2 which are randomly distributed in a cloud-like manner within the internal bone space 4a. In order that the internal bone space 4a is uniformly filled, the pressing device 9 is mounted after the first insertion of the support bodies 2, preferably the a point designated by 4c, in order to likewise supply support bodies 2 at this point.

Figure 18A:
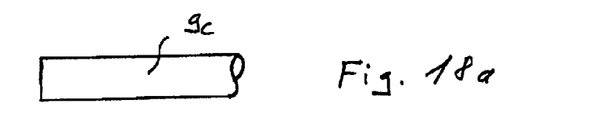
FIGS. 18a-18e differently designed plunger tips.
Figure 18B:
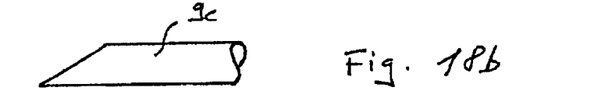
Figure 18C:
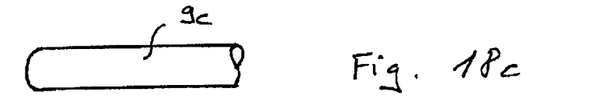
Figure 18D:
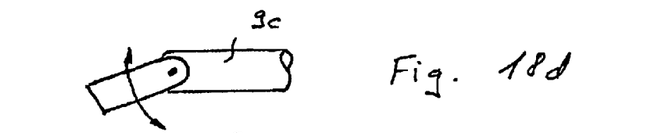
Figure 18E:
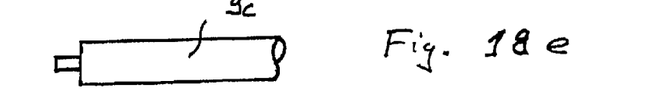

The plunger 9c can have markings 9e in order to monitor the depth of penetration of the plunger 9c. The length of the plunger 9c can be selected such that its front part can be introduced up to and into the internal bone space 4a, for example by up to a centimeter. The tip of the plunger 9c can, as shown in FIGS. 18a and 18b, be made flat or rounded. Such plungers are also termed compressing plungers. The supply device 5 preferably has a plurality of differently designed plungers 9c. For example the plunger 9c could have an obliquely extending tip as shown in FIG. 18b. This can serve to align or to shift support bodies 2 already arranged within the vertebral body 4. A plunger 9c of this kind can also be termed a positioning plunger. The position of the support bodies 2 in the vertebral body 4 can be made visible with the aid of an X-ray image so that a doctor can change or correct the support bodies 2 with correspondingly designed tools such as plungers, hooks or tongs. FIG. 18d shows a plunger 9c with a controllably arranged tip. FIG. 18e shows a plunger 9c with a projecting guide part which can for example engage into the hollow space 3 of a support body 2.

The pressing device 9 shown in FIG. 19 includes a force measuring device 9f with which the force produced in the direction of movement B is measured and is preferably also directly indicated. The force measuring device 9f can, for example, include a spring and also a display so that the doctor can directly measure the force exerted onto the support bodies 2. The force measuring device 9f can, for example, also be designed as an electronic apparatus including, for example, a piezo-crystal and also a display or an acoustic output, with the measured signal also being supplied to a monitoring device 11. The maximum force exerted on the support bodies 2 is preferably restricted. The force measurement provides an indication of the state of filling, for example the wedging of the support bodies. The pressing device 9 preferably includes a handle 9h.

The pressing device 9 could also include a drive 9g in order to bring about a force, blows or vibrations on the support bodies 2. In an advantageous method step a plurality of support bodies 2 is supplied to the internal bone space 4a and thereafter a vibrating force is exerted on the support bodies 2 in order to compress the support bodies 2 located in the internal bone space 4a and in order to thus obtain a high packing density and in order to thereby feed a large number of support bodies 2 to the internal bone space 4a. The frequency of vibration preferably lies in the range between 1 and 15000 Hz, in particular between 5 and 50 Hz.

In an advantageous embodiment the drive device 9g produces an elastic shock wave which is transferred into the plunger 9a which has the consequence that the length of the plunger 9a is varied, for example by +/−2 mm at a frequency of preferably between 1 and 50 Hz.

The drive device 9g could also be connected to a monitoring device 11 and the maximum force and/or the frequency and/or the stroke could be monitored.

Figure 20A:
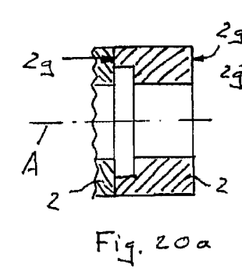
FIGS. 20a-20c longitudinal sections of differently shaped support bodies.
Figures 20B, 20C:
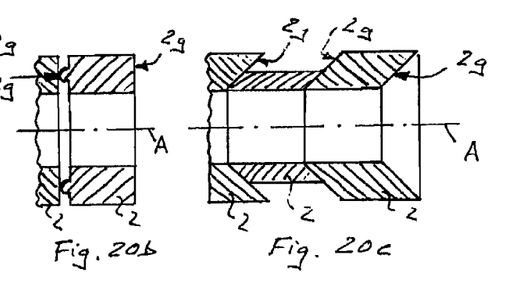

The FIGS. 20a to 20c show differently designed support bodies 2 with rounded or, for example, hexagonal outer contour in a longitudinal section along the axis A. In FIG. 20a the abutment locations 2g are designed as abutment surfaces, with the abutment locations 2g arranged at the left having a reduced support surface in comparison to the abutment locations 2g arranged at the right. The support bodies 2 illustrated in FIG. 20b have at the left-hand side a circular abutment 2g which extends fully in the peripheral direction. A plurality of individual projecting elements, for example hemispherically projecting elements, could also be arranged distributed in the peripheral direction, with each element forming an abutment location 2g. The support bodies 2 shown in FIG. 20c have abutment locations 2g which are designed as truncated cone-like surfaces. An advantage of this design is that the support bodies are mutually centered on displacement in the direction of the axis A. The support bodies 2 could also have different outer diameters as shown in FIG. 20c.

Figure 21:
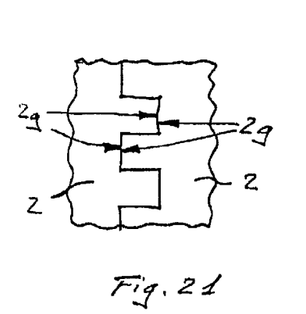
FIG. 21 a peripheral view of an abutment location.

FIG. 21 shows in an outside view a development of the abutment locations 2g between the two support bodies 2. These areally designed abutment locations 2g mutually engage within one another which prevent a mutual rotation of adjacent support bodies 2 as they are pushed in. The abutment locations 2g could also be of form-fitted design.

Figure 22A:
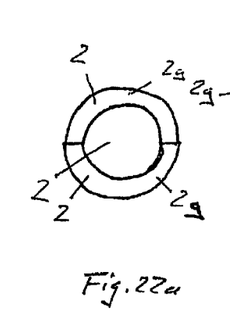
FIGS. 22a-b three individual support bodies arranged within one another.
Figure 22B:
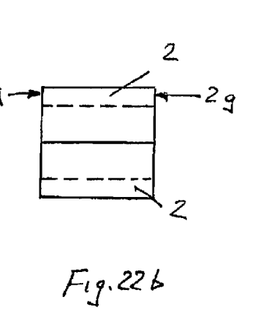

FIG. 22a shows in a side view three support bodies 2, two U-shaped support bodies 2, which surround a cylindrical support body 2. These three support bodies 2 are arranged in the cannula 6 in such a way that they can be supplied to the internal bone space 4a via the abutment locations in the direction of the axis A as shown in a side view in FIG. 22b, with the three support bodies 2 becoming randomly arranged within the internal bone space 4a since these are not mutually connected together.

The surface of the support body 2 located within the two U-shaped support bodies 2 can be of any desired shape and can for example also have edges or points, also at its end surfaces. The support bodies 2 shown in FIGS. 20a-20c and also 22a and 22b can, for example, be of circular or multi-cornered design radial to the axis A; or can also have tips, edges, cut-outs or apertures.

The end face of the plunger 9c can be designed in a plurality of shapes and can for example also have the end faces shown in FIGS. 20a to 20c.

FIG. 23 shows a further support body 2 with abutment surfaces 2g. The arms could be designed in a plurality of different forms with it having to be ensured that one abutment surface 2g or an abutment location 2g is present on the front side and also on the reverse side in each case.

The support bodies 2 shown in FIGS. 8a to 8d could have abutment locations 2g spaced apart in the direction of an axis A. For example, the support body 2 shown in FIG. 8b can have a self-centering abutment location 2g at the uppermost and lowermost tip as shown in FIG. 20c, so that a plurality of said support bodies 2, which are arranged behind one another in a cannula 6, which mutually contact each other at the abutment locations 2g, are displaceable in the direction of the axis A and can thus be fed to the internal bone space 4a.

The invention claimed is:

1. A dry flowable filler structure (1) for formation of a support structure in an internal bone space (4a), comprising a plurality of biocompatible support bodies (2) of identical shape which are not mutually connected and which are resistant to fracture against physiological loads occurring in the internal bone space (4a), the plurality of support bodies (2) being configured to allow independent and random arrangement in the internal bone space and having a size between 2 mm and 10 mm, and wherein the support bodies (2) have an axis (A) and two plane-shaped abutment locations (2g) oppositely disposed in the direction of the axis (A), wherein the support bodies (2) are configured to have a polyhedral outer contour with edges (2d) not being rounded and extending parallel to the axis (A) and to have a 3-edged to 10-edged outer shape with edges (2d) not being rounded, wherein at least one of the abutment locations has a recess (2c), and wherein the recess in at least one of the support bodies is configured to lockingly engage with at least a portion of an edge of the outer shape of another support body of the plurality of biocompatible support bodies (2), wherein the multi-edged outer shape is formed from a plurality of planar surfaces, and wherein the two abutment locations (2g) extend perpendicular to the axis (A), and further characterized in that the recess (2c) or an interior cavity (3) is filled with at least one of an osteo-inductive and an osteo-conductive substance.

2. A filler structure in accordance with claim 1, characterized in that the support bodies have a 6-edged outer shape.

3. A filler structure in accordance with claim 1, characterized in that the recess (2c) extends concentrically to the axis (A).

4. A filler structure in accordance with claim 1, characterized in that the support bodies (2) have an open inner hollow cavity (3) which opens into oppositely disposed recesses (2c).

5. A filler structure in accordance with claim 4, characterized in that the inner hollow cavity (3) is of cylindrical shape and extends in the direction of the axis (A).

6. A filler structure in accordance with claim 5, characterized in that each support body (2) takes up a total volume which includes the volume of a material of the support body (2) and its inner hollow cavity (3), with the volume of the inner cavity (3) amounting to more than 30% of the total volume.

7. A filler structure in accordance with claim 6, characterized in that the volume of the inner hollow cavity (3) amounts to more than 50% of the total volume.

8. A filler structure in accordance with claim 1, characterized in that all support bodies (2) are identically configured with respect to size and shape.

9. A filler structure in accordance with claim 1, characterized in that the recess (2) has notch-shaped blocking points (2h).

10. A filler structure in accordance with claim 1, characterized in that the edges (2d) have notch-shaped blocking points (2h).

11. A filler structure in accordance with claim 1, characterized in that the support bodies (2) have an outer diameter (D) and orthogonal to the outer diameter a height (H) in the direction of the axis (A) and in that the outer diameter (D) is at least 1.5 times the height (H).

12. A filler structure in accordance with claim 1, characterized in that the support bodies (2) have a surface shaped such that the surface of a support body (2) filled into the internal bone space (4a) projects into the recess (2c) of an adjacently disposed support body (2).

13. A filler structure in accordance with claim 12, characterized in that the surface and the recess (2c) of the support bodies (2) are shaped in a mutually fitting manner such that mutual wedging occurs between the surfaces projecting into the respective recesses (2c).

14. A filler structure in accordance with claim 13, characterized in that the wedging takes place in such a way that a cohesive self-stable support structure is formed within the internal bone space (4a).

15. A filler structure in accordance with claim 1, characterized in that the surface of the support bodies (2) have, with the exception of the abutment locations (2g), shapes selected from the group consisting of a corner, an edge, a peak, a recess, and an aperture.

16. A filler structure in accordance with claim 1, characterized in that the support body (2) has a cylindrical inner cavity (3) extending in the direction of the axis (A) which opens at both ends into the abutment location (2g).

17. A filler structure in accordance with claim 1, characterized in that the support bodies (2) consist of
ceramic materials selected from the group consisting of calcium phosphate/hydroxylapatite, aluminum oxide, zirconium oxide, ATZ ceramic (aluminum zirconium oxide), bioactive glasses, glass ceramic materials, and porcelain or
metallic materials selected from the group consisting of titanium, tantalum, stainless steel, steel alloys, and titanium alloys, or
polymers selected from the group consisting of polymethyl methacrylate (PMMA), polyetheretherketone (PEEK), polyethylene (PE), and polyethylene terephthalate (PET), or
biodegradable polymers.

18. A feeding device (5) for supplying of a filler structure (1) capable of dry flowing into an internal bone space (4a), with the filler structure (1) comprising non-spherical support bodies (2) with a size between 2 mm and 10 mm, wherein the support bodies (2) have two oppositely disposed and plane-shaped abutment locations that extend perpendicular to the axis (A) and that are (2g) spaced apart in the direction of an axis (A), and wherein the support bodies have a polyhedral outer contour with edges (2d) extending parallel to the axis (A), and wherein the feeding device (5) includes a cannula (6) that is configured such that a cross-section is matched to that of the size of the non-spherical support bodies (2) in such a way that the support bodies (2) can be supplied following one another within the cannula (6) aligned in the direction of the axis (A) to the internal bone space (4a) and with the feeding device (5) including a pressing device (9) having a plunger (9c) displaceable in the cannula (6) wherein the plunger is coupled to a driving apparatus that is configured to apply an elastic shockwave to the plunger (9c) to provide during feeding of the support bodies an elastic shockwave in the feeding direction on the support bodies (2) located within the cannula (6) in order to supply the support bodies (2) to the internal bone space (4a) and in order to supply the support bodies within the cannula and within the internal bone space (4a) with an elastic shockwave.

19. A feeding device in accordance with claim 18, wherein the pressing device (9) includes a force measuring device (9d) for the measuring of the thrust force acting on the support bodies (2) in the feeding direction.

20. A feeding device in accordance with claim 18, wherein the pressing device (9) includes a driving apparatus (9e) that is configured to allow driving of the plunger (9c) in the feeding direction.

21. A feeding device in accordance with claim 18, wherein the plunger (9c) has a length such that its front part can be introduced up to and into the internal bone space (4a).

22. A feeding device in accordance with claim 21 including a plunger (9c) having an obliquely extending tip and the plunger (9c) being rotatably arranged within the cannula (6) such that it can act on a filler structure (1) located within the internal cavity (4a) of the bone and change its position.

23. A method of feeding of a filler structure comprising a plurality of biocompatible support bodies (2) of identical shape which are not mutually connected and which are resistant to fracture against physiological loads occurring in the internal bone space (4a), the plurality of support bodies (2) being configured to allow independent and random arrangement in the internal bone space and having a size between 2 mm and 10 mm, and wherein the support bodies (2) have an axis (A) and two plane-shaped abutment locations (2g) oppositely disposed in the direction of the axis (A), wherein the support bodies (2) are configured to have a polyhedral outer contour with edges (2d) not being rounded and extending parallel to the axis (A) and to have a 3-edged to 10-edged outer shape with edges (2d) not being rounded, wherein at least one of the abutment locations has a recess (2c), and wherein the recess in at least one of the support bodies is configured to lockingly engage with at least a portion of an edge of the outer shape of another support body of the plurality of biocompatible support bodies (2), wherein the multi-edged outer shape is formed from a plurality of planar surfaces, and wherein the two abutment locations (2g) extend perpendicular to the axis (A), the method comprising a step in which the support bodies (2) are fed through a cannula, following one another with mutually oppositely disposed abutment locations (2g) by a thrust force acting in the feeding direction wherein the individual support bodies (2) are randomly and independently arranged in the internal bone space (4a), and further comprising a step of using a pressing device to provide an elastic shockwave to increase packing density and effect random distribution and interlocking of the support bodies, and still further comprising a step of feeding additional support bodies in the internal bone space.

24. A method in accordance with claim 23, characterized in that all support bodies (2) have the same shape, in that the support bodies (2) have recesses (2c) and in that the support bodies (2) are randomly arranged in the internal bone space (4a) in such a way that the surface of the support bodies project into the recess (2c) of adjacently disposed support bodies (2).

25. A method in accordance with claim 24, characterized in that the surface of support bodies (2) are wedged into the recess (2c) of adjacently disposed support bodies (2).

26. A method of filling of an internal cavity (4a) of a bone in which an internal bone space (4a) is opened, in which a plurality of non-spherical biocompatible support bodies (2) of identical shape which are not mutually connected and which are resistant to fracture against physiological loads occurring in the internal bone space (4aa), the plurality of support bodies (2) being configured to allow independent and random arrangement in the internal bone space and having a size between 2 mm and 10 mm, and wherein the support bodies (2) have an axis (A) and two plane-shaped abutment locations (2g) oppositely disposed in the direction of the axis (A), wherein the support bodies (2) are configured to have a polyhedral outer contour with edges (2d) not being rounded and extending parallel to the axis (A) and to have a 3-edged to 10-edged outer shape with edges (2d) not being rounded, wherein at least one of the abutment locations has a recess (2c), and wherein the recess in at least one of the support bodies is configured to lockingly engage with at least a portion of an edge of the outer shape of another support body of the plurality of biocompatible support bodies (2), wherein the multi-edged outer shape is formed from a plurality of planar surfaces, and wherein the two abutment locations (2g) extend perpendicular to the axis (A) are fed following one another, aligned in a defined position and contacting each other and under the action of force to the internal bone space (4a) and in which the support bodies (2) within the internal bone space (4a) come into contact with bone tissue, are randomly and independently arranged with respect to their position and are mutually wedged via engagement of a surface of one support body with a recess (2c) of an adjacently disposed support body, the method further comprising a step of using a pressing device to provide an elastic shockwave to increase packing density and effect random distribution and interlocking of the support bodies, and still further comprising a step of feeding additional support bodies in the internal bone space.

27. A method in accordance with claim 26, characterized in that a hollow cavity (4b) in the bone is first formed in the internal bone space (4a) and thereafter the support bodies (2) are fed to the hollow cavity (4b) of the bone.

28. A method in accordance with claim 26, characterized in that the support bodies (2) are fed under pressure and elastic shockwaves to the internal bone space (4a) in such a way that the support bodies (2a) form a hollow cavity (4b) of the bone or enlarge the bone.

29. A method in accordance with claim 26, characterized in that, following one another a plurality of times, a group of support bodies (2) is first fed to the inner space (4a) of the bone and thereafter support bodies (2) located in the internal bone space (4a) are compressed or aligned.

30. A method in accordance with claims 26, characterized in that the force which acts on the support bodies (2) during the feeding into the internal bone space (4a) is restricted to a predetermined maximum value.

31. A method in accordance with claims 26, characterized in that the support bodies (2) have an internal hollow cavity (3) and in that the internal hollow cavity (3) is filled with at least one of an osteo-inductive and an osteo-conductive substance prior to introduction of the support bodies (2).

32. A method in accordance with claims 26, characterized in that at least one of an osteo-inductive and an osteo-conductive substance is supplied to the internal bone space (4a) after all support bodies (2) have been introduced.

33. A kit for fixing and further enlargement of a partly fractured vertebral body including a plurality of non-spherical biocompatible support bodies (2) of identical shape which are not mutually connected and which are resistant to fracture against physiological loads occurring in the internal bone space (4a), the plurality of support bodies (2) being configured to allow independent and random arrangement in the internal bone space and having a size between 2 mm and 10 mm, and wherein the support bodies (2) have an axis (A) and two plane-shaped abutment locations (2g) oppositely disposed in the direction of the axis (A), wherein the support bodies (2) are configured to have a polyhedral outer contour with edges (2d) not being rounded and extending parallel to the axis (A) and to have a 3-edged to 10-edged outer shape with edges (2d) not being rounded, wherein at least one of the abutment locations has a recess (2c), and wherein the recess in at least one of the support bodies is configured to lockingly engage with at least a portion of an edge of the outer shape of another support body of the plurality of biocompatible support bodies (2), wherein the multi-edged outer shape is formed from a plurality of planar surfaces, and wherein the two abutment locations (2g) extend perpendicular to the axis (A), and a feeding device (5) including a cannula (6) having an internal cross-section matched to the size of the support bodies (2) such that the support bodies (2) can be fed within the cannula (6) following one another in the same aligned position and contacting one another mutually at the abutment locations (2g) to the internal bone space (4a) in the direction of the axis (A) and further comprising a plunger (9c) displaceable in the cannula (6) and configured to exert a force in the feeding direction (A) onto the rearmost of the support bodies (2) located in the cannula (6), and still further comprising a driving apparatus (9e) that applies an elastic shockwave to the plunger (9c) during feeding of the support bodies.

* * * * *

UNITED STATES PATENT AND TRADEMARK OFFICE
CERTIFICATE OF CORRECTION

PATENT NO.        : 7,993,402 B2                                            Page 1 of 1
APPLICATION NO.   : 11/572035
DATED             : August 9, 2011
INVENTOR(S)       : Bruno Sidler It is certified that error appears in the above-identified patent and that said Letters Patent is hereby corrected as shown below:

On title page, item 73 Assignee,
replace "Hkross AG"
with "Akross AG."

Signed and Sealed this
Twenty-fourth Day of July, 2012

David J. Kappos
*Director of the United States Patent and Trademark Office*